United States Patent [19]
Silver

[11] Patent Number: 5,542,934
[45] Date of Patent: Aug. 6, 1996

[54] MULTIPLE CARPULE HYPODERMIC SYRINGE

[76] Inventor: Richard M. Silver, 33 Holly La., Ashland, Mass. 01721

[21] Appl. No.: 458,565

[22] Filed: Jun. 2, 1995

[51] Int. Cl.$^6$ ........................................... A61M 5/00
[52] U.S. Cl. ........................................... 604/191; 604/232
[58] Field of Search ........................................... 604/191, 187, 604/218, 232, 87, 88

[56] References Cited

U.S. PATENT DOCUMENTS

| | | | |
|---|---|---|---|
| 3,767,085 | 10/1973 | Cannon et al. | 604/191 X |
| 4,333,457 | 6/1982 | Margulies | 604/232 |
| 4,710,178 | 12/1987 | Leonard et al. | 604/232 X |
| 5,137,528 | 8/1992 | Crose | 604/232 X |
| 5,314,412 | 5/1994 | Rex | 604/191 |

*Primary Examiner*—John D. Yasko
*Attorney, Agent, or Firm*—Brian M. Dingman

[57] ABSTRACT

A hypodermic syringe designed to simultaneously dispense anesthetic liquid from a plurality of carpules. In a preferred embodiment, the syringe comprises a body which includes a pair of parallel, open-ended, generally cylindrical members and a base member. The cylindrical members are partially inserted into and fixedly secured within the base member. Each cylindrical member is shaped to include an elongated chamber adapted to removably receive therewithin an anesthetic liquid-containing carpule. The base member is externally-shaped to define a finger-gripping handle. The syringe also includes a fluid mixing chamber for receiving fluid drawn from each of the carpules through a corresponding fluid transport assembly mounted within the open top end of the respective cylindrical member, the fluid mixing chamber being formed by the mating engagement of an externally-threaded disk and an internally-threaded cap. The disk has a pair of openings into which the respective top ends of the cylindrical members are partially inserted. The cap is provided with a threaded boss over which a hypodermic needle assembly may be removably mounted, the hypodermic needle being used to deliver the fluid from the fluid mixing chamber to a patient. The syringe further includes a plunger for emptying the entire contents of both carpules into the fluid mixing chamber at the same time in a single plunger stroke.

6 Claims, 5 Drawing Sheets

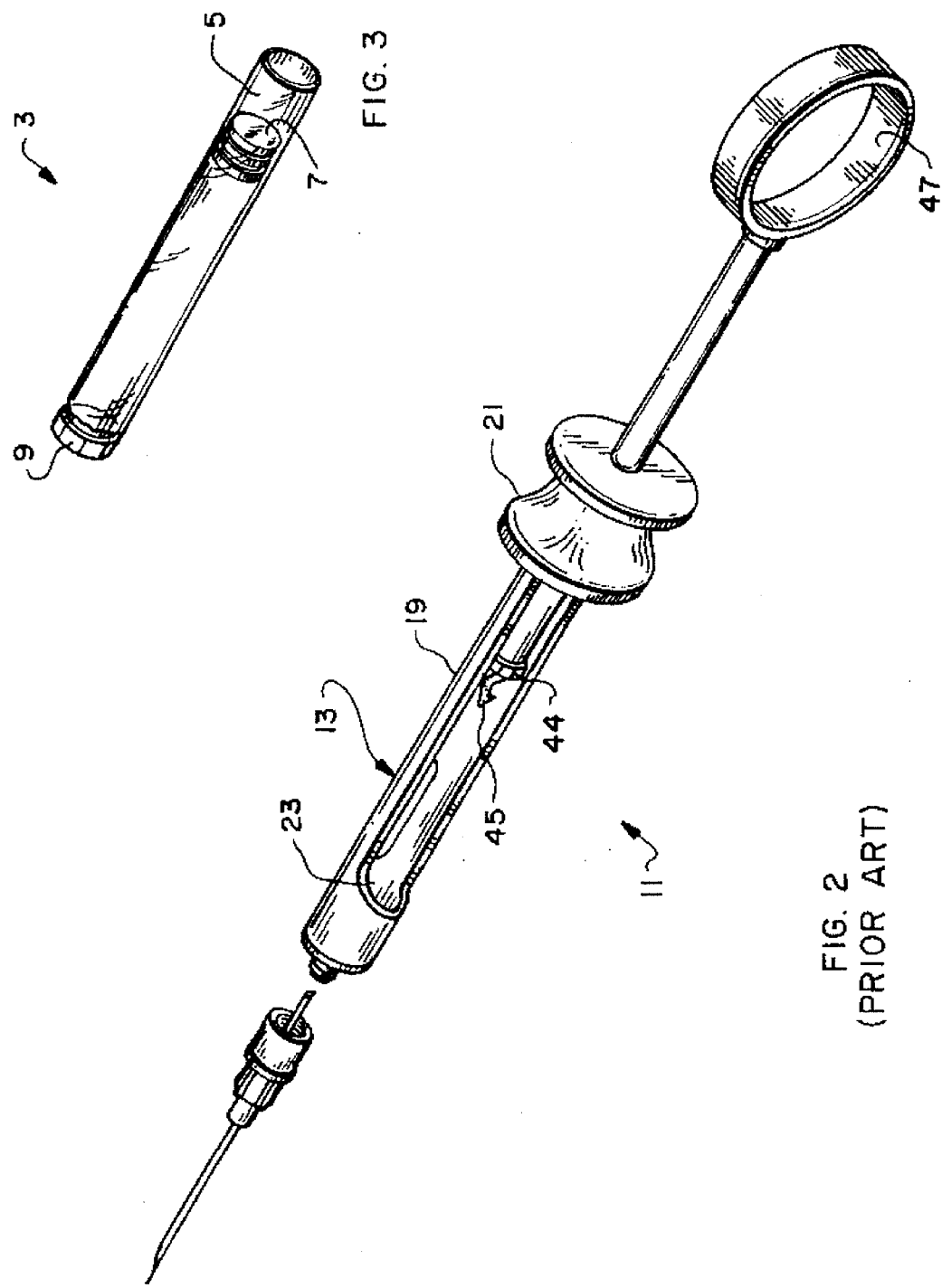

MULTIPLE CARPULE HYPODERMIC SYRINGE

BACKGROUND OF THE INVENTION

The present invention relates generally to syringes and more particularly to hypodermic syringes.

Syringes are commonly used, for example in the fields of medicine and dentistry, to deliver controlled quantities of fluids, typically liquids, to desired locations. One common type of syringe used in both medicine and dentistry is the hypodermic syringe. Hypodermic syringes are designed for the subcutaneous administration of fluids to a patient in need thereof and typically comprise an elongated body, a plunger and a hypodermic needle. In one well-known type of hypodermic syringe, the elongated body is substantially hollow and the plunger is slidably mounted within the elongated body from one end thereof, the elongated body and the plunger together defining a fluid-tight reservoir. The hypodermic needle is mounted on the end of the elongated body opposite the plunger, the hypodermic needle being in fluid communication with the reservoir through a small orifice formed in the elongated body. Typically, to load the above-described hypodermic syringe with a desired liquid, the hypodermic needle is inserted into a supply of the desired liquid while the plunger is in a depressed position; the plunger is then pulled outwardly, thereby drawing the liquid into the reservoir through the hypodermic needle. Thereafter, to dispense the fluid from the syringe into a patient's tissue, the hypodermic needle is inserted into the tissue and the plunger is depressed.

Another well-known type of hypodermic syringe is shown in FIGS. 1 and 2 herein and is represented generally by reference numeral 11. Syringe 11 is specifically designed for dispensing fluid from a certain type of fluid container referred to in the art as a "carpule." An example of a carpule is illustratively shown in FIG. 3 and represented generally therein by reference numeral 3, carpule 3 comprising a cylindrically-shaped tube 5 having one end sealed with a slidably mounted plug 7 and the other end sealed with a puncturable cap 9.

Referring back now to FIGS. 1 and 2, syringe 11 can be seen to include a body 13. Body 13, in turn, includes a hollow, generally cylindrical member 19 and an hourglass shaped base member (or handle) 21, cylindrical member 19 being partially inserted into and fixedly secured within a longitudinally extending bore 31 formed in base member 21.

Member 19, which is shaped to define a chamber 20 adapted to removably receive a carpule, has an internally-treaded open top end 27 and an open bottom end 29. An externally-threaded boss 30 provided with a longitudinal bore 32 is partially inserted into top end 27 of member 19 and removably mounted therewithin. A large oval-shaped opening 23 is provided on one side of member 19 through which a carpule may be inserted into or removed from chamber 20. A small oval-shaped opening 25 is provided on member 19 opposite opening 23 to permit access to chamber 20 so as to facilitate the removal of a carpule from chamber 20 through opening 23.

A small opening 33 is provided in the bottom end of member 21 to permit access to bore 31, bore 31 extending from the top of base member 21 to just above the bottom thereof.

Syringe 11 also includes a platform 35 of annular shape which is slidably mounted within that portion of member 19 that is disposed within bore 31. (Further upward movement of platform 35 into that portion of member 19 not disposed within bore 31 is prevented by a slight narrowing in the cross-sectional diameter of member 19.) Platform 35 is used to support the bottom of a carpule disposed within chamber 20. Platform 35 itself rests upon a spring 37 also disposed within that portion of member 19 located within bore 31. To facilitate the insertion and removal of a carpule into chamber 20, platform 35 may be lowered within member 19 by pushing platform 35 downwardly against spring 37, thereby compressing spring 37.

Syringe 11 also includes a plunger 41. Plunger 41 comprises an elongated stem 43 which extends upwardly through opening 33 of member 21 and is adapted for slidable axial movement within member 19. The top end of stem 43 is shaped to include a flange 44 which is adapted to engage an inner lip 36 formed on platform 35 for use in pushing platform 35 downwardly against spring 37. Plunger 41 also comprises a harpoon 45 fixedly mounted on the top of flange 44. Harpoon 45 is used to engage the slidably mounted plug of a carpule loaded in chamber 20. Plunger 41 further comprises a ring 47, which is fixedly mounted on the bottom end of stem 43. Ring 47 is adapted to receive the thumb or finger of a user for use in sliding stem 43 axially within member 19.

Syringe 11 further includes a hypodermic needle assembly 51. Needle assembly 51 includes a base 53 and a hypodermic needle 55. Base 53 is internally-threaded so as to be threadingly mounted on boss 30. Hypodermic needle 55 is fixedly mounted in base 53, with its lower end extending down through base 53 into chamber 20 so as to puncture the puncturable cap of a carpule present within chamber 20 and so as to receive fluid from the carpule when plunger 41 is depressed.

To use syringe 11 to dispense liquid from a carpule, one first loads the desired carpule into syringe 11. This loading step may be done by pulling down on ring 47 of plunger 41 so as to lower platform 35 within member 19 while, at the same time, inserting the lower end of the carpule into chamber 20 through opening 23. When platform 35 is sufficiently lowered, the entire carpule is capable of fitting into place within chamber 20. Plunger 41 is then released, causing platform 35 to return back to its normal position and causing the top cap of the carpule to be punctured by the bottom end of needle 55. To dispense the liquid contained within the carpule through needle 55, one presses plunger 41 upwardly. This causes harpoon 45 to engage the slidably mounted plug in the carpule and push it upwardly, thereby forcing the contents of the carpule out through needle 55.

One application of hypodermic syringe 11 in dentistry is in the administration of anesthetic liquids, such as LIDOCAINE, to dental tissues prior to certain dental procedures. Typically, such anesthetic liquids are packaged in standard-sized carpules containing about 1.8 ml of fluid. Unfortunately, such a quantity of anesthetic fluid is typically insufficient to appropriately anesthetize a patient. Accordingly, to administer the necessary quantity of anesthetic fluid to a patient, a dental care provider frequently must repeat, as necessary, the steps of loading a single carpule into the hypodermic syringe and then dispensing the contents of the carpule into the patient's dental tissue. As can readily be appreciated, it can be quite cumbersome for the dental care provider to have to repeat the steps of loading a single carpule and then dispensing its contents for a multiplicity of carpules. Moreover, the foregoing routine also requires that, for each carpule used, the dental care provider must "stick" the patient with the hypodermic needle (and, thereafter, aspirate to ensure that the needle has not hit a blood vessel).

Accordingly, the present inventor has identified a need for a hypodermic syringe which is capable of holding a plurality of anesthetic fluid carpules at one time and which is capable of dispensing the contents of said plurality of carpules without requiring multiple needle sticks (assuming that the needle has not hit a blood vessel).

In U.S. Pat No. 3,767,085, inventors Cannon et al., which issued Oct. 23, 1973, and which is herein incorporated by reference, there is disclosed a double barrel carpule type syringe having, at its discharge end, a common mixing and dispensing chamber provided with a rotary agitator driven from a motor on the syringe. One barrel of the carpule contains an elastomeric base material and the other an accelerator therefor. The syringe has a double plunger by means of which the base material and the accelerator are simultaneously discharged into the chamber in prescribed proportions as the mixed material is discharged from the end of the chamber. The mixing chamber assembly and the carpule assembly are readily removable from the body of the syringe.

In U.S. Pat No. 4,367,737, inventors Kozam et al., which issued Jan. 11, 1983, and which is herein incorporated by reference, there is disclosed a multiple barrel syringe for selective delivery of two different types of fluids. The syringe comprises a body having a pair of bores each containing a plunger and each terminating in a smaller sized conduit for receiving fluid from the bores. Connected to the body is a movable member having a single conduit or passage and a needle mounted on the member and communicating with the bore. The movable member may be manually actuated to bring its single conduit into communication with a selected bore conduit for providing passage of fluid from the selected bore to the needle. The movable member may then be moved to another position to bring the needle into communication with the other bore. Sealing means are provided on the movable member to avoid leakage and feedback of fluid from or to the bore not dispensing fluid.

In U.S. Pat. No. 4,874,368, inventors Miller et al., which issued Oct. 17, 1989, and which is herein incorporated by reference, there is disclosed an improved fibrin glue delivery system. The delivery system comprises a pair of syringe tubes, which can be actuated by plungers simultaneously or independently, a connecting member which holds the syringe tubes in parallel alignment and a unique needle assembly which ensures the components in the syringe bodies will not be commingled until they reach the treatment site. The unique needle assembly also permits the user to manipulate the needles to enhance visibility when the surgeon is working through a speculum or when direct access is difficult. One of the syringe tubes contains fibrinogen and the other syringe tube contains thrombin.

In U.S. Pat. No. 5,290,259, inventor Fischer, which issued Mar. 1, 1994, and which is herein incorporated by reference, there is disclosed a double syringe delivery system for holding a pair of syringes in a manner so as to accommodate the simultaneous activation of the plunger of each syringe in order to effect simultaneous delivery of the contents of each syringe, each syringe containing different contents. The double syringe delivery system includes an elongated support member that is placed between the barrel of each syringe. The elongated support member has resilient, C-shaped clamps on opposite sides of the support member. The clamps are used for holding the syringe barrels of both syringes so that the syringe barrels will be held together in a parallel manner. Further, elongated support member and clamps hold the syringe barrels in a fashion that is slightly longitudinally offset from one another to permit the two syringe barrels to be held together as closely as possible. An interconnecting bridge member connects the two syringe plungers so that they can also be simultaneously activated even though they are also slightly longitudinally offset from one another.

In U.S. Pat. No. 5,354,284, inventors Haber et al., which issued Oct. 11, 1994, and which is herein incorporated by reference, there is disclosed a multiple injection syringe system having a cartridge carrier that is loaded with three pre-filled cartridges which are to be selectively accessed so that the contents of the cartridges can be delivered to a patient in a particular, predetermined order. The syringe system of the present invention has particular application to facilitating the SASH process, such that two of the cartridges are filled with saline and one with heparin. A double ended needle cannula is carried by a rotatable manifold. One end of the cannula projects outwardly from the manifold for administering an injection, while the opposite end projects inwardly to communicate with a selected cartridge within the carrier. The manifold is rotated around the cartridge carrier to each of three positions corresponding to three steps of the SASH process, whereby the cannula is correspondingly rotated from one cartridge to the next. Fluid from the selected cartridge is expulsed via the cannula by applying to said cartridge a hydraulic pressure that is generated by driving a piston through a fluid filled cylinder.

SUMMARY OF THE INVENTION

It is an object of the present invention to provide a novel hypodermic syringe.

It is another object of the present invention to provide a novel hypodermic syringe of the type that is well-suited for dispensing fluid from a carpule, i.e., a fluid container comprising a generally cylindrical tube having one end sealed with a slidably mounted plug and the other end sealed with a puncturable cap.

It is yet another object of the present invention to provide a novel hypodermic syringe that is well-suited for dispensing anesthetic liquid, such as LIDOCAINE, from a carpule.

It is still another object of the present invention to provide a hypodermic syringe as described above that is well-suited for dispensing anesthetic liquid from a standardsized carpule having a volume of about 1.8 ml.

It is still yet another object of the present invention to provide a hypodermic syringe as described above that is capable of simultaneously holding a plurality of carpules.

It is a further object of the present invention to provide a hypodermic syringe as described above that is capable of simultaneously dispensing the contents of two or more carpules.

It is still a further object of the present invention to provide a hypodermic syringe as described above that is capable of simultaneously dispensing the entire contents of two or more carpules with a single plunger stroke.

It is still yet a further object of the present invention to provide a hypodermic syringe as described above that is easy to manufacture and use.

Additional objects, as well as features and advantages, of the present invention will be set forth in part in the detailed description which follows, and in part will be obvious from the detailed description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that changes may be made without departing from the scope of the invention. The following detailed description is, therefore, not to be taken in a limiting sense, and the scope of the present invention is best defined by the appended claims.

In furtherance of the above and other objects to be described or to become apparent from the description below, a hypodermic syringe constructed according to the teachings of the present invention broadly comprises (a) a hypodermic needle; (b) means for holding a plurality of fluid-containing carpules; and (c) means for simultaneously dispensing the contents of at least two of said plurality of fluid-containing carpules through said hypodermic needle.

The present invention is also directed to a method of administering anesthetic liquid to a patient in need thereof, said method broadly comprising the steps of: (a) providing a hypodermic syringe, said hypodermic syringe comprising (i) a hypodermic needle, (ii) means for holding a plurality of fluid-containing carpules, and (iii) means for simultaneously dispensing the contents of at least two of said plurality of fluid-containing carpules through said hypodermic needle; (b) loading a plurality of anesthetic liquid-containing carpules into said hypodermic syringe; (c) inserting the hypodermic needle of said hypodermic syringe into an appropriate area of the patient in need of anesthetic liquid; and (d) simultaneously dispensing the contents of at least two of said plurality of anesthetic liquid-containing carpules through the hypodermic needle and into the patient in need thereof.

BRIEF DESCRIPTION OF THE DRAWINGS

The accompanying drawings, which are hereby incorporated into and constitute a part of this specification, illustrate the preferred embodiments of the invention and, together with the description, serve to explain the principles of the invention. In the drawings wherein like reference numerals represent like parts:

FIG. 2 is a partially exploded perspective view of the prior art hypodermic syringe shown in FIG. 1;

FIG. 3 is a perspective view of a conventional anesthetic liquid-containing carpule;

DETAILED DESCRIPTION OF A PREFERRED EMBODIMENT

Figure 1:
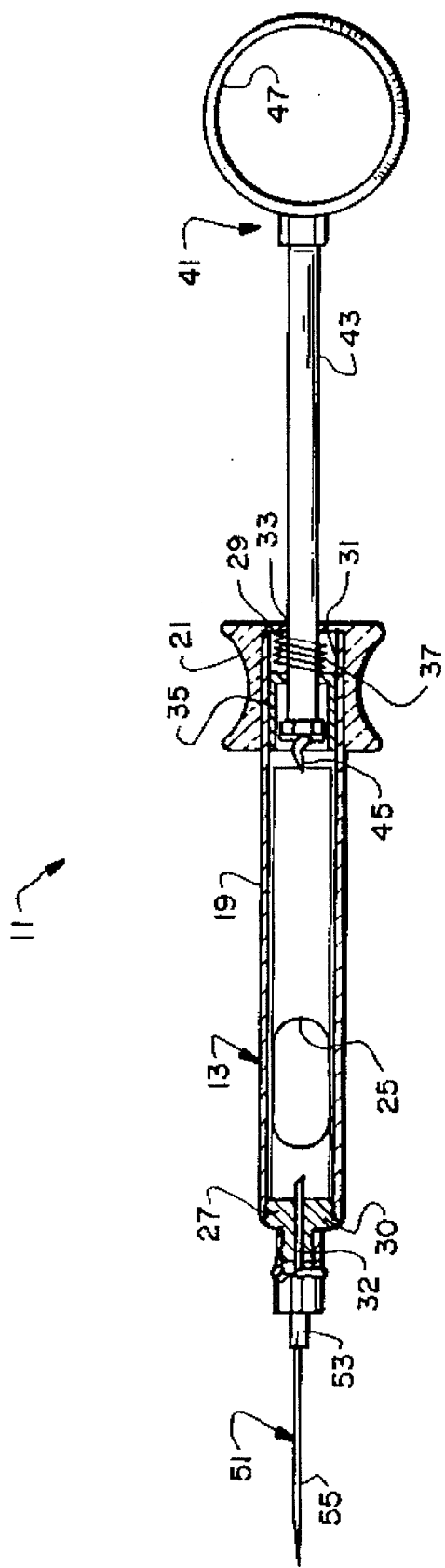
FIG. 1 is a section view of a prior art hypodermic syringe useful in the subcutaneous dispensing of anesthetic liquid from an anesthetic liquid-containing carpule.
Figure 4:
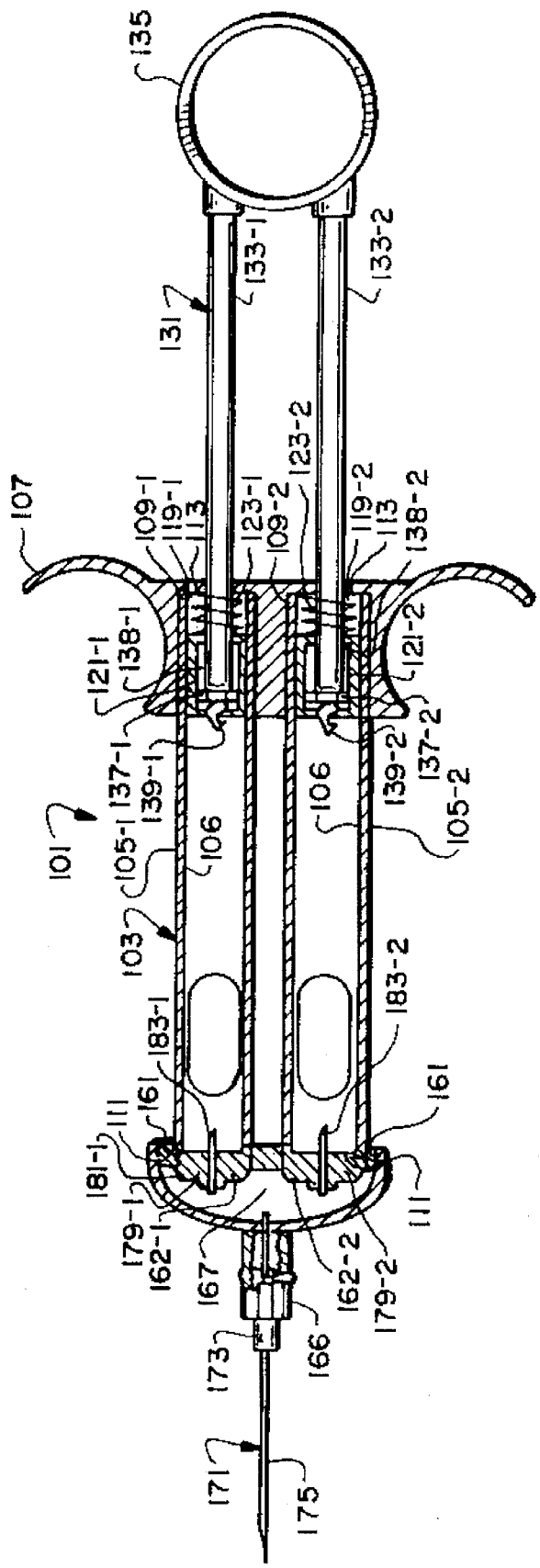
FIG. 4 is a section view of one embodiment of a hypodermic syringe constructed according to the teachings of the present invention for use in the subcutaneous dispensing of anesthetic liquid from a plurality of anesthetic liquid-containing carpules.
Figure 5:
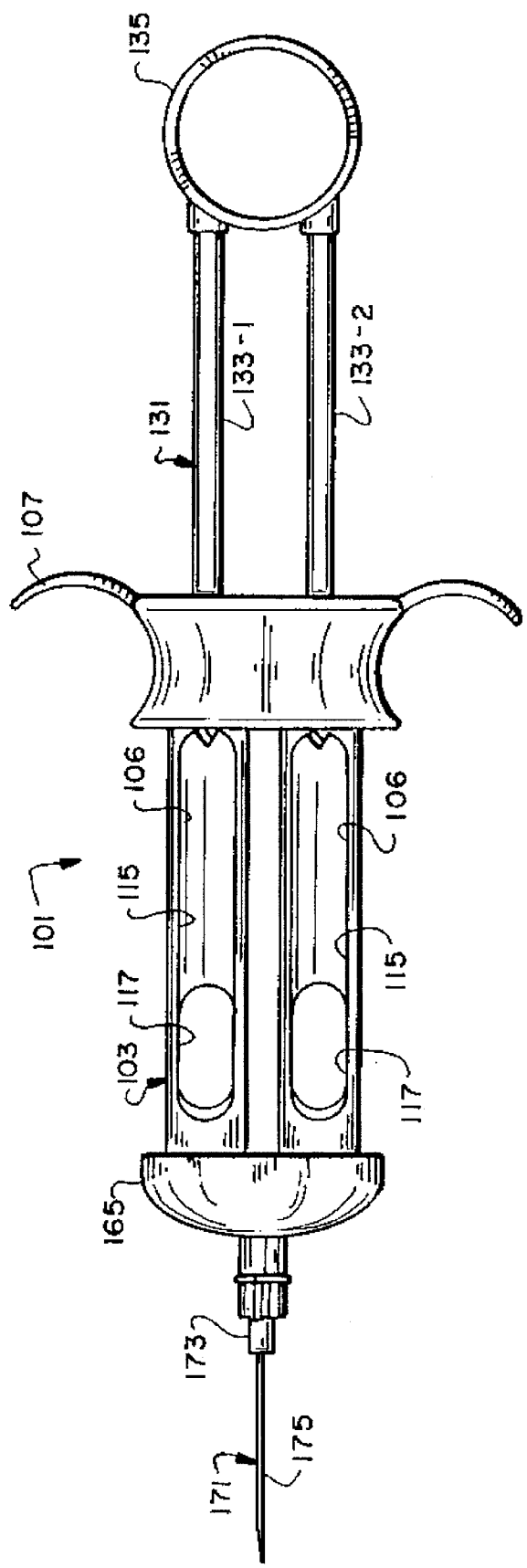
FIG. 5 is a front view of the hypodermic syringe shown in FIG. 4.

Referring now to FIGS. 4 through 7, there are shown various views of one embodiment of a hypodermic syringe adapted for use in the subcutaneous dispensing of anesthetic liquid from a plurality of anesthetic liquid-containing carpules to a patient in need thereof, said hypodermic syringe being constructed according to the teachings of the present invention and being represented generally by reference numeral 101.

Syringe 101 comprises a body 103, which is preferably made of metal (e.g., stainless steel) or another similarly suitable material. Body 103 includes a pair of parallel, generally cylindrical members 105-1 and 105-2 and a base member or handle 107. Handle 107 is provided with a pair of parallel, longitudinally-extending bores 109-1 and 109-2 which extend from the top of handle 107 to just short of the bottom thereof, members 105-1 and 105-2 being partially inserted into and fixedly secured within bores 109-1 and 109-2, respectively. A pair of small orifices 119-1 and 119-2 are formed on the bottom of handle 107 for use in accessing bores 109-1 and 109-2, respectively.

Members 105-1 and 105-2 are identical to one another and to member 19 of syringe 101, each member 105 being hollow and shaped to define a chamber 106 adapted to removably receive therewithin a conventional carpule containing 1.8 ml of anesthetic liquid. Each member 105 has an open internally-threaded top end 111, an open bottom end 113, a large oval-shaped opening 115 and a small oval-shaped opening 117. As with openings 23 and 25 of prior art syringe 11, openings 115 and 117 of syringe 101 extend longitudinally on opposite sides of member 105 and are used in the insertion and removal of a carpule into and out of chamber 106.

Syringe 101 also includes a pair of platforms 121-1 and 121-2 and a pair of springs 123-1 and 123-2, platforms 121 and springs 123 being identical to platform 35 and spring 37, respectively, of syringe 11 and being mounted within members 105-1 and 105-2 in the same manner in which platform 35 and spring 37 are mounted within member 19 of syringe 11.

Syringe 101 further includes a plunger 131, plunger 131 comprising a pair of stems 133-1 and 133-2. A ring 135, which is adapted to receive the thumb or finger of a user for use in sliding plunger 131, is disposed at a first end of stems 133-1 and 133-2 and mechanically couples together stems 133-1 and 133-2. The opposite ends of stems 133-1 and 133-2 are inserted into members 105-1 and 105-2, respectively, through orifices 119-1 and 119-2, respectively, and terminate in a corresponding pair of flanges 137-1 and 137-2. Flanges 137-1 and 137-2, like flange 44 of syringe 11, are adapted to engage the inner lips 138-1 and 138-2 of platforms 121-1 and 121-2, respectively, for use in pushing platforms 121 downwardly against their corresponding springs 123. Plunger 131 further includes a pair of harpoons 139-1 and 139-2, which are fixedly mounted on the respective top surfaces of flanges 137-1 and 137-2. Harpoons 139-1 and 139-2, in a manner similar to that performed by harpoon 45 of syringe 11, are used to simultaneously engage the slidably mounted plugs of a pair of carpules disposed within chambers 20-1 and 20-2 so as to urge said plugs upwardly towards their corresponding puncturable caps.

Figure 6:
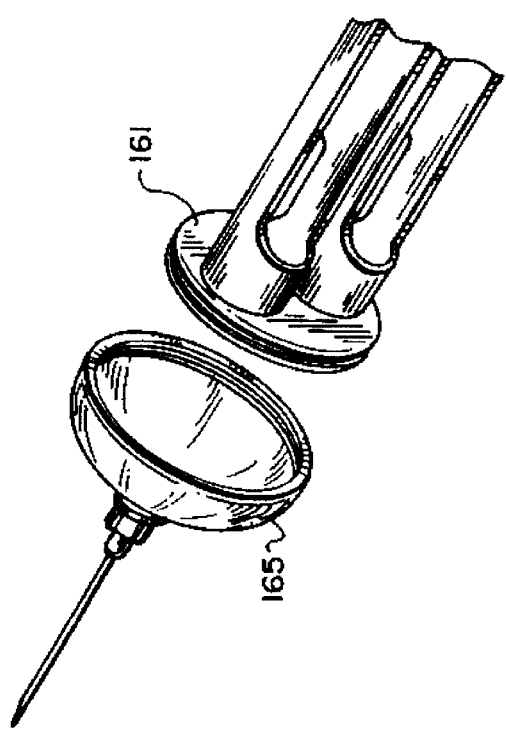
FIG. 6 is a fragmentary partially exploded perspective view of the hypodermic syringe of FIG. 4.
Figure 7:
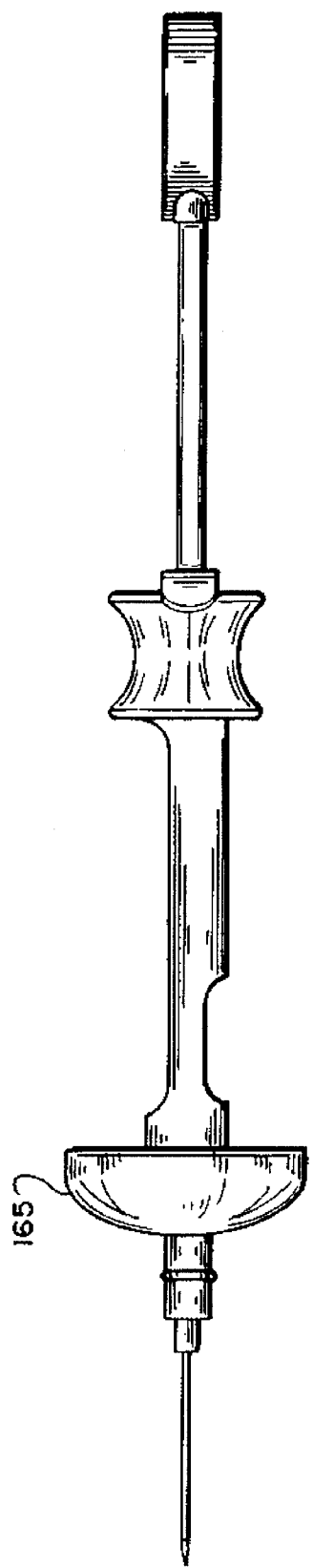
FIG. 7 is a side view of the hypodermic syringe shown in FIG. 4.

As seen best in FIG. 6, syringe 101 further comprises an externally-threaded disk 161, disk 161 preferably being made of metal or another similarly suitable material and being provided with a pair of openings 162-1 and 162-2. The top portions of members 105-1 and 105-2 are partially inserted into openings 162-1 and 162-2, respectively, and are secured to disk 161 by welding or other suitable means. An internally-threaded cap 165 is removably screwed onto disk 161, cap 165 and disk 161 together defining a fluid mixing chamber 167. The top of cap 165 is provided with an externally-threaded, hollow boss 166 which opens into chamber 167 and which is used to removably mount thereon a hypodermic needle assembly 171. Needle assembly 171 is identical to needle assembly 51 of syringe 11 and includes a base 173 and a hypodermic needle 175. Base 173 is internally-threaded so as to be threadingly removably received on boss 166. Hypodermic needle 175 is fixedly mounted in base 173 and extends outwardly from both sides thereof, the lower end of needle 175 extending down into chamber 167 so as to receive fluid from chamber 167 when plunger 131 is depressed.

Syringe 101 further comprises a pair of fluid transport assemblies 179-1 and 179-2. Each fluid transport assembly 179 comprises an externally-threaded disk-shaped base 181 and a hypodermic needle 183 mounted in base 181 and extending outwardly from both sides thereof. Bases 181-1 and 181-2 are adapted to be screwed into open top ends 111-1 and 111-2 of members 105-1 and 105-2, respectively. Fluid transport assemblies 179-1 and 179-2 serve a dual purpose, namely, to puncture the puncturable caps of a pair of carpules located in chambers 20-1 and 20-2 and to fluidly interconnect said carpules with chamber 167 so that, when plunger 131 is depressed, the contents of the carpules are simultaneously forced through needles 183-1 and 183-2 into chamber 167.

Syringe 101 is loaded and used in much the same fashion as is syringe 11. To load syringe 101 with a pair of carpules, one pulls down on ring 135 of plunger 131 to lower platforms 121-1 and 121-2 and, at the same time, inserts the lower ends of a pair of carpules into chambers 106-1 and 106-2. When platforms 121 are sufficiently lowered, each carpule is capable of fitting into place within its respective chamber 106. Plunger 131 is then released, causing platforms 121-1 and 121-2 to return back to their normal positions and causing the top puncturable caps of the carpules to be punctured by the bottom ends of needles 183-1 and 183-2, respectively. Then, to dispense the contents of the pair of carpules, one presses plunger 131 upwardly. This causes harpoons 139-1 and 139-2 to simultaneously engage the slidably mounted plugs in the pair of carpules and push them upwardly at the same time, thereby forcing the contents of the carpules first through needles 183-1 and 183-2 into chamber 167 and then from chamber 137 out through needle 175.

As can readily be appreciated, one advantage to syringe 101, as compared to syringe 11, is that the contents of two carpules may be simultaneously dispensed through the same hypodermic needle with a single plunger stroke and one needle "stick."

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A large volume delivery hypodermic syringe for simultaneously dispensing liquid from a plurality of liquid-containing carpules into a patient, comprising:

a body including a plurality of elongated, parallel chambers, each adapted to removably receive therein a carpule;

an externally-threaded disk covering one end of all of said chambers;

an internally-threaded cap received on the external threads of said disk, to define a fluid chamber for receiving fluid from carpules in said parallel chambers;

a like plurality of fluid passageways passing through said disk and aligned with said chambers, for transporting fluid from said carpules into said fluid chamber;

a hypodermic needle-receiving member coupled to said cap for holding a hypodermic needle;

a fluid channel passing through said cap and into said needle-receiving member to transport fluid from said fluid chamber into a hypodermic needle held in said needle-receiving member; and means for simultaneously discharging liquid from carpules in said parallel chambers, through said passageways, said fluid chamber and said fluid channel, to provide the liquid into the hypodermic needle for delivery into a patient.

2. The syringe of claim 1 in which said fluid passageways are carried by fluid transport assemblies inserted into the ends of said parallel chambers, where said parallel chambers meet said disk.

3. The syringe of claim 1 in which said cap is concave and rounded.

4. The hypodermic syringe as claimed in claim 1 wherein each of said carpules includes a slidably mounted plug and wherein said discharging means comprises a plunger, said plunger including a plurality of harpoons, each of said harpoons being adapted to move a slidably mounted plug for one of the pair of carpules.

5. The hypodermic syringe as claimed in claim 1 wherein each of said carpules has a puncturable cap at its top end, said hypodermic syringe further comprising means for puncturing said puncturable caps.

6. The hypodermic syringe as claimed in claim 1 wherein said body also includes a handle.

\* \* \* \* \*